United States Patent
Perry

(10) Patent No.: US 9,511,014 B2
(45) Date of Patent: *Dec. 6, 2016

(54) SYNTHETIC SOLID CLEANSER

(71) Applicant: Arthur William Perry, Belle Mead, NJ (US)

(72) Inventor: Arthur William Perry, Belle Mead, NJ (US)

(73) Assignee: DR. PERRY SKINDUSTRIES, LLC, Belle Meade, NJ (US)

( * ) Notice: Subject to any disclaimer, the term of this patent is extended or adjusted under 35 U.S.C. 154(b) by 36 days.

This patent is subject to a terminal disclaimer.

(21) Appl. No.: 14/575,248

(22) Filed: Dec. 18, 2014

(65) Prior Publication Data

US 2015/0104530 A1    Apr. 16, 2015

Related U.S. Application Data

(63) Continuation of application No. 13/972,830, filed on Aug. 21, 2013, now Pat. No. 8,933,007.

(51) Int. Cl.
| | |
|---|---|
| A61K 8/97 | (2006.01) |
| A61Q 19/10 | (2006.01) |
| A61K 8/02 | (2006.01) |
| A61K 8/36 | (2006.01) |
| C11D 3/04 | (2006.01) |
| C11D 3/20 | (2006.01) |
| C11D 3/382 | (2006.01) |
| C11D 17/00 | (2006.01) |
| C11D 3/48 | (2006.01) |
| A61K 8/34 | (2006.01) |
| A61K 8/92 | (2006.01) |

(52) U.S. Cl.
CPC .............. *A61K 8/97* (2013.01); *A61K 8/0216* (2013.01); *A61K 8/347* (2013.01); *A61K 8/361* (2013.01); *A61K 8/922* (2013.01); *A61K 8/927* (2013.01); *A61Q 19/10* (2013.01); *C11D 3/046* (2013.01); *C11D 3/2079* (2013.01); *C11D 3/382* (2013.01); *C11D 3/48* (2013.01); *C11D 17/003* (2013.01); *C11D 17/006* (2013.01)

(58) Field of Classification Search
None
See application file for complete search history.

(56) References Cited

U.S. PATENT DOCUMENTS

| | | |
|---|---|---|
| 7,381,692 B2 | 6/2008 | Grissett et al. |
| 8,680,031 B1 | 3/2014 | Poli |
| 2004/0147189 A1 | 7/2004 | Smith et al. |
| 2005/0201965 A1 | 9/2005 | Kuhlman et al. |
| 2006/0002883 A1 | 1/2006 | Morikis et al. |
| 2012/0064136 A1* | 3/2012 | Baker et al. .................. 424/401 |

FOREIGN PATENT DOCUMENTS

WO    WO 2013/188942    12/2013

* cited by examiner

*Primary Examiner* — Necholus Ogden, Jr.
(74) *Attorney, Agent, or Firm* — Seyfarth Shaw LLP

(57) ABSTRACT

The present invention relates to a synthetic solid bar cleanser formulated to clean human skin. More particularly, the present invention relates to synthetic solid cleanser formulations which have pH of about 5.5, the same as human skin, and yet which perform similarly, or superior, to traditional soap.

20 Claims, No Drawings

SYNTHETIC SOLID CLEANSER

CROSS-REFERENCE TO RELATED APPLICATIONS

The present application is a continuation of U.S. application Ser. No. 13/972,830, filed Aug. 21, 2013, the disclosure of which is incorporated by reference herein in its entirety.

FIELD OF THE INVENTION

The present invention relates to a synthetic solid bar cleanser formulated to clean human skin. More particularly, the present invention relates to synthetic solid cleanser formulations which have pH of about 5.5, the same as human skin, and yet which perform similarly, or superior, to traditional soap.

BACKGROUND OF THE INVENTION

Soaps have been known and used for personal hygiene for thousands of years. Commonly referred to as toilet or bath bars, soaps for personal bathing and hand and face washing have been prepared from proprietary formulations of sodium and potassium soaps of fatty acids containing about 8 to 20 carbon atoms and other ingredients which improve the texture, appearance, and cleaning performance of bars. Plasticizing agents, perfumes and/or deodorants, antimicrobial agents, inert inorganic fillers or builders and other surfactants are commonly added.

While the body's physiologic pH is 7.4, the skin's physiologic pH is 5.5. Maintenance of the skin's normal pH is critical for the health of the skin. Disruption of the pH by typical soaps results in reduced barrier function of the stratum corneum, and create a more favorable environment for pathogenic bacteria.[1] Alkaline soaps alter the pH of the skin, from a physiologic 5.5 to the level of the soap, which may higher than 10. This results in an injury to the barrier function of the skin, increased susceptibility to environmental irritants and antigens, skin irritation with erythema and edema, reduction of water content and smoothness of the skin, and an alteration of the physiologic bactericidal and fungicidal capabilities of skin.[2] Chronic use of alkaline soaps is associated with more irritation than acidic syndets.[3] Specifically, alkaline soaps cause swelling of the stratum corneum, affecting both structural proteins and lipid matrix.[4] Alterations in skin pH play a role in the pathogenesis of irritant contact dermatitis, atopic dermatitis, ichthyosis, acne vulgaris and *Candida albicans* infections. The use of skin cleansers with the pH of 5.5 may prevent and treat those skin diseases[5] and aid in wound healing.[6]

Traditional alkaline soaps, alkali salts of fatty acids, are the predominant skin cleaner on the market. These significantly increase the pH of the skin while acidic skin cleaners do not significantly alter the pH.[7] Cleansers with pH of 5.5 do not interfere with the microflora of the skin and irritate the skin less than alkaline soaps.[8]

In clinical studies, acidic cleansers are less irritating than alkaline soaps[9] and can improve the disease state of contact dermatitis. Acidic cleansers reduce the levels of *Staphylococcus aureus* and *Candida* yeast on the skin[10,11]

Preservatives are typical toxic components of skin care products. 14% of the population is allergic to one or another preservative[12] manifesting as contact dermatitis which injures the barrier function of skin and sets up a condition that increases the toxicity of other skin care components, in addition, many preservatives are proven endocrine disrupters and suspected carcinogens.[13] As used in this specification, "performance" in bar skin cleaners is a function of skin cleaning ability, lather, "slip" (slide of the bar across the skin), and bar integrity.

Generally prepared from sodium and potassium fatty acid mixtures derived from natural fats and oils such as tallow, coconut oil, palm oil, palm kernel oil, soybean oil and the like, sodium fatty acid soaps are usually harder than potassium fatty acid soaps, and soaps of saturated fatty acids are harder than those prepared from unsaturated fatty acids. Accordingly, the hardness of fatty acid soaps increases with the length of the fatty chain. Most commercial toilet soap bars contain major amounts of sodium soaps of saturated fatty acid mixtures with minor amounts of potassium soaps and unsaturated fatty acid soaps to alter the feel, texture, appearance and wearability or resistance to cracking and discoloration of the bar. Petrolatum is a commonly used binding agent that helps hold the bar together. Petrolatum is an oil-based product with polycyclic aromatic hydrocarbons that have been implicated in carcinogenesis. Harsh surfactants such as sodium lauryl sulfate (SLS) are commonly used to improve performance, particularly "lather". SLS is a skin irritant for 100% of humans.

Due to these disadvantages, there has been a trend in the industry to manufacture toilet bars from blends of sodium and/or potassium soaps and compounds classified in the art as synthetic detergents ("syndets") or surfactants. There are also many commercially available bars prepared from these synthetic detergent compounds entirely devoid of the traditional fatty acid soaps. See for example U.S. Pat. Nos. 2,894,912; 2,781,320; 3,154,494; 3,186,948; 3,223,645; 3,224,976; 3,226,330. The specific compositions of many synthetic detergent and soap-synthetic detergent bars, usually referred to as combination bars in the industry, vary greatly, the majority of formulations being proprietary to the particular manufacturer.

In part, because the detergent industry has sought to produce toilet bars having improved appearance, texture, feel, scent, color and wearability acceptable to most consumers, they have ignored one of the most basic requirements for soap to be used on human skin: that is the skin's natural pH of 5.5 and inherent barrier oils and properties. Soap with a pH over 7 disturbs the natural anti-bacterial properties of sebum allowing for a proliferation of bacteria and yeast, particularly *S. aureus* and *P. aeruginosa*. This elevation of pH can last as long as 6 hours before natural homeostatic processes return the skin's natural pH to 5.5. Hence use of an alkaline facial scrub can actually promote bacterial proliferation and acne.

Some formulators have sought to produce synthetic detergents (referred to hereafter as "syndets") which are non-alkaline, preservative free, and contain no dyes, yet which provide the performance, i.e. feel, scent, froth and color, of traditional soaps. Unfortunately, providing a cleanser which froths and is still non-alkaline has been heretofore unachievable without resorting to the use of sodium lauryl sulfate (hereafter referred to as "SLS"), relatives thereof, and other irritating surfactants to achieve the frothing which consumers associate with good cleansing. Application of SLS and other similar surfactants on the skin can degrade the "barrier function" of the skin. The consequences of this are increased penetration of toxins that can damage the skin, the body as a whole, and have been shown to cause the skin to produce sebum and other oils as well as local inflammation that are anathema to achieving the healthiest skin possible.

DETAILED DESCRIPTION OF THE INVENTION

Exemplary embodiments of the present invention, result in very nonirritating, physiologically perfect, skin cleaner. Because it does not disturb the pH of the skin and also does not injure the "barrier function" of the skin, it renders the skin more physiologically impervious to the various toxins that skin is exposed to daily. These include environmental pollutants and also cosmetic products that are toxic to the skin. A syndrome of skin toxicity, largely due to soap toxicity, includes a slight redness, and a slight swelling of the skin, and enlarged, visible, pores. So many people have this problem, for so many years, that they think that that appearance is the innate characteristic of their skin. But when their exposure to skin cleansing products containing skin irritants is eliminated, and the cleansers of the present invention are initiated in a daily regimen, their skin is permitted to "detox" and its appearance and actual health improves. Exemplary embodiments of the present invention are beneficial when used alone, but are even more effective and have an overall synergistic effect when used as part of the system of skin rejuvenators which are the subjects of my co-pending patent applications. By using a more physiologic cleaner which, like the present invention, has the correct pH and without irritants, a patient achieves clean, healthy, pH-balanced skin which will allow for better penetration and utilization of the active agents in this and the other components of my skin rejuvenation system.

Irritants include the majority of commonly used surfactants, including SLS and sodium laureth sulfate and dozens more. Other irritants include various fragrances and preservatives which are common causes of contact dermatitis. These substances are avoided by formulations designed according to the teachings of the present invention.

Elimination of preservatives is a notable advantage of this invention. The exemplary embodiment was designed as a solid, which does not promote the growth of bacteria. Lemon and thyme oils are natural antibacterials and antifungals that further suppress the growth of bacteria and fungus in bar cleansers of the present invention.

Exemplary embodiments of the disclosed invention are syndet formulations that perform well. Specifically, they provide a skin cleansing bar which creates froth volume that consumers associate with good cleansing, and at a pH in a range of from 5.3 to about 5.8, preferably of 5.5. Typical syndets perform abysmally, creating a paltry amount of lather and a perception by a typical user that the cleaning ability is similarly minimal. Furthermore, the formulations of the present invention produce a "synthetic" cleanser for skin that is substantially free of skin irritants that can cause local inflammation and skin irritation, without actually promoting the growth of bacteria and fungi. The non-inflammatory ingredients of the present formulations provide a soothing experience with a pleasant texture and color. The formulations have a pleasing scent provided by ingredients that also have antioxidant, antifungal and antibacterial properties.

The skin cleanser of the present invention is a vegetable-based syndet bar. There are no animal products used in the creation of the skin cleanser of the present invention. The pH is the same as normal skin—i.e. in a range of from pH 5.3 to about pH 5.8 but preferably about pH 5.5. As a synthetic cleansing bar, the base has been formulated to meet this precise pH.

The skin cleanser of the present invention contains a variety of unique ingredients that improve the performance of the bar. Of note is that this bar is free of preservatives. The following listing of ingredients are provided as an exemplary, but non-limiting, embodiment of the present invention which is then formed into bars, as described hereinbelow.

| INGREDIENT | % by weight |
| --- | --- |
| Sodium Cocoyl Isethionate | 40-50%% |
| Stearic Acid | 30-40% |
| Water (Aqua) | 6-8%% |
| Cocamidopropyl Hydroxysultaine | 2-4% |
| Beeswax | 1-3% |
| Sodium Isethionate | 1-3% |
| *Citrus Limon* (Lemon) Peel Oil | 0.5-2% |
| *Avena Sativa* (Oat) Kernel Flour | 0.5-2% |
| Glycerin | 0.5-2% |
| Sodium Chloride | 0.5-1% |
| Titanium Dioxide (CI 77891) | 0.5-1% |
| *Lavandula Angustifolia* (Lavender) Oil | 0.01-1% |
| *Quillaja Saponaria* Bark Extract | .01-1% |
| *Thymus Vulgaris* (Thyme) Flower/Leaf Oil | .001-1% |

Elimination of preservatives is a notable advantage of this invention. The exemplary embodiment cleansers are designed as a solid, which do not promote the growth of bacteria. Lemon and thyme oils are natural antibacterials that further suppress the growth of bacteria in the cleansers of the present invention (see references below in ingredient section).

Superior performance—"Performance" in bar skin cleansers is a function of skin cleaning ability, lather, "slip", and bar integrity.

The present invention substituted common toxic surfactants with the coconut derived sodium cocoyl isethionate, cocamidopropyl hydroxysultaine, and sodium isethionate, substances that are milder skin cleaners[14] that help remove excess oil and dirt from the skin.

Unique mixture of ingredients—To accomplish the characteristic look, feel, smell, and performance of the present invention, a specific mixture of ingredients was used.

*Quillaja saponaria* bark extract, also known as soap bark, is a key ingredient in the present invention. *Quillaja* is a food additive that creates foam for carbonated drinks such as root beer and is the substance that gives a solid cleanser bar formulated according to the present invention its unique frothiness. *Quillaja* extract is purified extract of outer cambium layer of *quillaja saponaria* molina tree and contains natural nonionic surfactants called saponins that stabilize foams and emulsions.[15] Saponins are detergent-like substances showing antibacterial, antiviral, antitrichomonal, and antifungal activity. The antiviral properties have been demonstrated against rotavirus, *vaccinia* virus, herpes simplex virus type 1, *varicella zoster* virus, human immunodeficiency viruses 1 and 2 (HIV-1, HIV-2) and reovirus. *Quillaja* inhibits infection from host cells by preventing attachment and replication of virus[16] [17] [18]. In addition, it inhibits fungal growth,[19] [20] and has anti-Staphylococcal properties.[21] *Quillaja saponaria* has anti-*Trichomonas vaginalis* activity and inhibits mosquito larval development.[22] [23] It is also anti-inflammatory,[24] and an antioxidant[25] The combination of frothing ability as well as antibacterial, antiviral, anti trichomonal, and antifungal properties make *quillaja* an ideal agent for solid cleanser bars formulated according to the present invention, providing performance enhancement as well as antimicrobial qualities.

Other naturally occurring frothing agents include *Yucca saponin*, which also is included in this patent and imparts similar qualities to soap and foods.

Ground oats—this substance imparts a homogenous white color and "body" to the syndet and gives it a soothing feel. Ground oats have moisturization qualities,[26] and are anti-inflammatory and antihistaminic. The avenanthramides, a component of whole oat grain, are responsible for many of these effects. Avenanthramides inhibit the activity of nuclear factor kappaB and the release of proinflammatory cytokines and histamine, mechanisms in the pathophysiology of inflammatory dermatoses. Natural colloidal oatmeal helps restore the skin barrier and can improve atopic dermatitis and other conditions.[27][28]

Avenanthramides are phenolic compounds present in oats at approximately 300 parts per million (ppm) and exhibit anti-oxidant[29] and potent anti-inflammatory activity that are responsible for the anti-irritant effects of oats.[30]

Glycerin—This humectant provides the physical sensation of "slip", as opposed to "friction" when the bar is moved against the skin. The right amount of "slip" is necessary for an aesthetically pleasing experience. In addition, glycerin protects against irritants, accelerates recovery of irritated skin, increases water content of skin[31][32], and decreases symptoms of atopic dermatitis[33]. The diverse actions of the polyol glycerol on the epidermis include improvement of stratum corneum hydration, skin barrier function and skin mechanical properties, inhibition of the stratum corneum lipid phase transition, protection against irritating stimuli, enhancement of desmosomal degradation, and acceleration of wound-healing processes. Additionally, an antimicrobial effect has been demonstrated. Topical application of glycerol-containing products improves skin properties in diseases characterized by xerosis and impaired epidermal barrier function, such as atopic dermatitis. The increase of epidermal hydration by glycerol is critical in skin conditions aggravated by dry and cold environmental conditions, e.g. winter xerosis.

Beeswax—Soaps and syndets are mixtures of a variety of chemicals and will separate spontaneously as they age, causing a physical crumbling of the bar. To maintain bar integrity, most soaps contain petrolatum, an oil based product and suspected carcinogen[34][35]. The formulation for syndets of the present invention substitutes natural beeswax to maintain the integrity of the bar. Beeswax has a pleasant natural scent and is so nontoxic that it is actually edible, comprising the delicacy known as honeycomb.

*Thymus Vulgaris* Flower/Leaf Oil (Thyme)—a natural antioxidant[36][37] which also has antibacterial and antifungal properties. In concentrations of 3%, thyme essential oil healed fungal infections.[38] Thyme inhibits the growth of *Staphylococcus, Enterococcus, Escherichia*, and *Pseudomonas* bacteria, including multidrug resistant varieties.[39] It has also been shown to have antimicrobial properties against *Klebsiella* and *Strep agalactiae* bacteria. The antimicrobial activity of thyme is not trivial in fact it is stronger than that of the commonly used synthetic BHT.[40] Thyme has also been shown to cure leishmaniasis.[41] Thyme oil, particularly pungent, is an important component in the fragrance mixture of the exemplary embodiment.

Bergaptene-Free Essential Lemon Oil—This aromatherapy agent imparts part of the unique fragrance, along with lavender and thyme. Common lemon oil is a photosensitizer,[42] but bergaptene-free lemon oil, has all or substantially of the photosensitizing agent, bergaptene, removed, thereby eliminating most of the photosensitizing effect of lemon oil.

Lemon oil is also a natural antibacterial. *Staphylococcus aureus, Pseudomonas aeruginosa, Oenococcus* and *lactobacillus* bacteria,[43][44][45] *Candida* and *Aspergillis* fungus are all also killed by lemon and lavender oils.[46] Interestingly, lemon essential oil and thyme essential oil naturally repel mosquitoes, probably because they are toxic to mosquito larvae.[47]

Essential lemon oil enhances the penetration of vitamins E, A (retinyl acetate), and C (Ascorbic acid), important components of the inventor's patent pending day cream and evening serum regimens.[48]

Essential lemon oil has strong antioxidant activity and, in particular, significantly increases the antioxidative potential of the skin.[49][50]

Essential Lavender Oil—one of only two aromatherapy agents (the other being lemon oil) that have proven ability to lower blood pressure and heart rate.[51][52] These essential oils are natural mood elevators, and are released into the air during use of the product. Both lemon and lavender oils have been shown to improve cognitive function in Alzheimer's dementia patients.[53] Lavender and lemon oils have anxiolytic and antidepressant effects by suppressing dopamine activity in the brain.[54]

Lavender oil not only is safe, but is also antimutagenic.[55]

The exemplary embodiments of the present invention take advantage of the natural antibacterial and antifungal properties of lavender, lemon, and thyme oils, obviating the need for synthetic or other potentially skin-irritating or sensitizing preservatives.

Fragrance—The unique fragrance of syndets formulated according to the present invention is a result of the blend of lemon, lavender, and thyme oils.

Syndet Forming Process Description

The listed raw materials are blended together, checked to ensure the pH level is between 5.3 and 5.8 and preferably at pH 5.5, in a mix tank under proprietary conditions. The resultant molten synthetic hatch is filtered and pumped onto a roll, to convert the molten material to a thin solid, the syndet. The solid syndet is scraped from the roll and conveyed to a pelletizer. The pelletizer converts the syndet into a noodle form that is placed in a super sack for storage and handling. Further processing is done by placing the syndet noodles into an amalgamator and mixing with final product ingredients such as fragrances or other additives. The resultant mass is milled and extruded into billets. The billets are then pressed into finished bars and packaged as the finished product.

Non-Primary Irritant and Non-Primary Sensitizer—The non-irritant and non-sensitizing status of the cleanser of the exemplary embodiment was appraised using a Repeat Insult Patch Test. When the exemplary embodiment cleanser having the formulation described hereinabove was applied to 50 human subjects under semi-occlusion at a 10% dilution in distilled water, in accordance with the industry reference *Appraisal of the Safety of Chemicals in Food, Drugs, and Cosmetics*, published by The Association of Food and Drug Officials of The United States, 1965 (modified), no irritation or sensitization was observed in any of the subjects. Each subject bad 9 discrete 24-hour exposures over a period of three weeks and no reactions or adverse events were observed.

[1] Acta Derm VenereoL 2013 May; 93(3):261-7. Skin pH: from basic science to basic skin care. Ali S M, Yosipovitch G.

[2] Int J Dermatol. 2002 August; 41(8):494-9. Correlation between pH and irritant effect of cleansers marketed for dry skin. Baranda L, González-Amaro R, Torres-Alvarez B, Alvarez C, Ramirez V.

[3] Skin Res Technol. 2001 May; 7(2):98-104. A comparative study of the effects on the skin of a classical bar soap and a syndet cleansing bar in normal use conditions and in the soap chamber test. Barel A O, Lambrecht R, Clarys P, Morrison B M Jr, Paye M.

[4] Int J Cosmet Sci. 2003 June; 25(3): 103-12. pH-induced alterations in stratum corneum properties. Ananthapadmanabhan K P, Lips A, Vincent C, Meyer F, Caso S, Johnson A, Subramanyan K, Vethamuthu M, Rattinger G, Moore D J.

[5] Skin Pharmacol Physiol. 2006; 19(6):296-302. The pH of the skin surface and its impact on the barrier function. Schmid-Wendtner M H, Korting H C.

[6] Am J Clin Dermatol. 2002; 3(4):261-72. The acidic milieu of the horny layer: new findings on the physiology and pathophysiology of skin pH. Rippke F, Schreiner V, Schwanitz H J.

[7] Dermatology. 1997; 195(3):258-62. Effects of soap and detergents on skin surface pH, stratum corneum hydration and fat content in infants. Gfatter R, Hackl P, Braun F.

[8] *Dermatology.* 1995; 191 (4):276-80. The concept of the acid mantle of the skin: its relevance for the choice of skin cleansers. Schmid M H, Korting H C.

[9] Skin Res Technol. 2001 May; 7(2):98-104. A comparative study of the effects on the skin of a classical bar soap and a syndet cleansing bar in normal use conditions and in the soap chamber test. Barel A O, Lambrecht R, Clarys P, Morrison B M Jr, Paye M.

[10] Acta Derm Venereol 80; 421-4. 2000. Experimental *candida albicans* lesions in healthy humans: dependence on Skin pH. Runernan B et al.

[11] Dermatology. 1995; 191(4):276-80. The concept of the acid mantle of the skin: its relevance for the choice of skin cleansers. Schmid M H, Korting H C.

[12] Am J Clin Dermatol. 2004; 5(5):327-37. Cosmetic allergy: incidence, diagnosis, and management. Orton D I, Wilkinson J D.

[13] Journal of Environmental and Public Health. Volume 2012, Article ID 713696, 52 pages. Review Article Endocrine-Disrupting Chemicals: Associated Disorders and Mechanisms of Action. Sam De Coster and Nicolas van Larebeke

[14] *Contact Dermatitis.* 1999 June; 40(6):316-22. Irritancy ranking of anionic detergents using one-time occlusive, repeated occlusive and repeated open tests. Tupker R A, Bunte E E, Fidler V, Wiechers J W, Coenraads P J.

[15] Cutan Ocul Toxicol. 2007; 26(3):227-33.Antioxidant activities of essential oil mixtures toward skin lipid squalene oxidized by UV irradiation. Wei A, Shibamoto T.

[16] Future Med Chem. 2010 July; 2(7): 1083-97. Prevention of rotavirus infections in vitro with aqueous extracts of *Quillaja Saponaria* Molina. Roner M R, Tam K I, Kesling-Barrager M.

[17] Antiviral Res. 2011 June; 90(3):231-41. Characterization of in vivo anti-rotavirus activities of saponin extracts from *Quillaja saponaria* Molina. Tam K I, Roner M R.

[18] *J Gen Virol,* 2007 January; 88(Pt 1):275-85. Antiviral activity obtained from aqueous extracts of the Chilean soap bark tree (*Quillaja saponaria* Molina). Roner M R, Sprayberry J, Spinks M, Dhanji S.

[19] *Arch Environ Contam Toxicol.* 2010 October; 59(3): 417-23. Growth inhibition of regenerated cellulose nanofibrous membranes containing *Quillaja* saponin. Dixit V, Tewari J, Obendorf S K.

[20] Arch Environ Contam Toxicol 2010 October; 59(3): 417-23. 6. Fungal growth inhibition of regenerated cellulose nanofibrous membranes containing *Quillaja saponin*. Dixit V, Tewari J, Obendorf S K.

[21] Appl Biochem Biotechnol. 2010 October; 162(4):1008-17. Hemolytic and antimicrobial activities differ among saponin-rich extracts from guar, *quillaja, yucca*, and soybean. Hassan S M, Byrd J A, Cartwright A L, Bailey C A.

[22] J Ethnopharmacol. 2002 August; 81(3):407-9. The use of commercial saponin from *Quillaja saponaria* bark as a natural larvicidal agent against *Aedes aegypti* and *Culex pipiens*. Pelah D. Abramovich Z, Markus A, Wiesman Z.

[23] Parasitol Res. 2012 June; 110(6):2551-6. Anti-*Trichomonas vaginalis* activity of saponins from *Quillaja, Passiflora*, and *Ilex* species. Rocha T D, de Brum Vieira P, Gnoatto S C, Tasca T, Gosmann G.

[24] J Pharm Pharmacol. 2011 May; 63(5):718-24. Topical anti-inflammatory activity of quillaic acid from *Quillaja saponaria* Mol. and some derivatives, Rodriguez-Diaz M, Delporte C, Cartagena C, Cassel B K, González P, Silva X, León F, Wessjohann L A.

[25] *J Diabetes Complications.* 2008 September-October; 22(5); 348-56. The effects of *Yucca sehidigera* and *Quillaja saponaria* on DNA damage, protein oxidation, lipid peroxidation, and some biochemical parameters in streptozotocin-induced diabetic rats, Fidan A E, Dündar Y.

[26] *Clin Cosmet Investig Dermatol.* 2012; 5:183-93. Safety and efficacy of personal care products containing colloidal oatmeal. Criquet M, Roure R, Dayan L, Nollent V, Bertin C.

[27] J Drugs Dermatol 2010 September; 9(9):1116-20. Mechanism of action and clinical benefits of colloidal oatmeal for dermatologic practice. Cerio R, Dohil M, Jenine D, Magina S, Mahé E, Stratigos A J.

[28] *Cutis.* 2007 December; 80(6 Suppl):2-16. Natural advances in eczema care. Eichenfield L F, Fowler J F Jr, Rigel D S, Taylor S C.

[29] Indian J Dermatol Venereol Leprol. 2012 March-April; 78(2):142-5. Oatmeal in dermatology: a brief review. Pazyar N, Yaghoobi R, Kazerouni A, Feily A.

[30] Arch Dermatol Res. 2008 November; 300(10):569-74. Avenanthramides, polyphenols from oats, exhibit anti-inflammatory and anti-itch activity. Sur R, Nigam A, Grote D, Liebel F, Southall M D.

[31] Skin Pharmacol Physiol 2006; 19(4):207-15. An in vivo randomized study of human skin moisturization by a new confocal Raman fiber-optic microprobe: assessment of a glycerol-based hydration cream, Chrit L, Bastien P, Sockalingum G D, Batisse D, Leroy F, Manfait M, Hadjur C.

[32] Arch Dermatol Res. 2010 August; 302(6):435-41. Effects of glycerol on human skin damaged by acute sodium lauryl sulphate treatment. Atrux-Tallau N, Romagny C, Padois K, Denis A, Haftek M, Falson F, Pirot F, Maibach H I.

[33] Skin Pharmacol Physiol. 2012; 25(3):155-61. Noninvasive sNoninvasive stratum corneum sampling and electron microscopical examination of skin barrier integrity: pilot study with a topical glycerin formulation for atopic dermatitis. Daehnhardt-Pfeiffer S, Surber C, Wilhelm K P, Daehnhardt D, Springmann G, Boettcher M, Foelster-Holst R.

[34]*Occup Med.* 1988 July-September; 3(3):475-94. The carcinogenic potential of selected petroleum-derived products. Rothman N, Emmett E A.

[35]*Appl Occup Environ Hyg.* 2003 November; 18(11):890-901. Petroleum mineral oil refining and evaluation of cancer hazard. Mackerer C R, Griffis L C, Grabowski Jr J S, Reitman F A.

[36]Cutan Ocul Toxical. 2007; 26(3):227-33. Antioxidant activities of essential oil mixtures toward skin lipid squalene oxidized by UV irradiation, Wei A, Shibamoto T.

[37]Food Chem. 2013 December 1; 141(3):2198-206. Effects of *Salvia officinalis* and *Thymus vulgaris* on oxidant-induced DNA damage and antioxidant status in HepG2 cells. Kozics K, Klusová V, Srančiková A, Mučaji P, Slameňová D, Hunáková L, Kusznierewicz B, Horváthová E.

[38]Int J Dermatol. 2012 July; 51(7):790-5. Researching accessible and affordable treatment for common dermatological problems in developing countries. An Ethiopian experience. Shimelis N D, Asticcioli S, Baraldo M, Tirillini B, Lulekal E, Murgia V.

[39]Microb Drug Resist. 2012 April; 18(2):137-48. The antimicrobial activity of thyme essential oil against multidrug resistant clinical bacterial strains. Sienkiewicz M, Lysakowska M, Denys P, Kowalczyk E.

[40]Roum Arch Microbiol Immunol. 2012 April-June; 71(2):61-9. In vitro antimicrobial and antioxidant activity of black thyme (*Thymbra spicata* L.) essential oils. Saidi M, Ghafourian S, Zarin-Abaadi M, Movahedi K, Sadeghifard N.

[41]J Vector Borne Dis. 2008 December; 45(4):301-6. Comparison of *Thymus vulgaris* (Thyme), *Achillea millefolium* (Yarrow) and propolis hydroalcoholic extracts versus systemic glucantime in the treatment of cutaneous leishmaniasis in balb/c mice. Nilforoushzadeh M A, Shirani-Bidabadi L, Zolfaghari-Baghbaderani A, Saberi S, Siadat A H, Mahmoudi M.

[42]*Arch Dermatol Res.* 1985; 278(1):31-6. A study of the phototoxicity of lemon oil. Naganuma M, Hirose S, Nakayama Y, Nakajima K, Someya T.

[43]J Food Prot.2007 January; 70(1):114-8. Use of lemon extract to inhibit the growth of malolactic bacteria, Conte A, Sinigaglia M, Del Nobile M A.

[44]World J Microbial Biotechnol 2013 July; 29(7):1161-7. Effect of citrus lemon oil on growth and adherence of *Streptococcus mutans*. Liu Y, Zhang X, Wang Y, Chen F, Yu Z, Wang L, Chen S, Guo M.

[45]J Food Prot. 2007 January; 70(1): 114-8. Use of lemon extract to inhibit the growth of malolactic bacteria. Conte A, Sinigaglia M, Del Nobile M A.

[46]J Appl Microbiol. 2009 December 1; 107(6): 1903-11. Antimicrobial activity of lavender, tea tree and lemon oils in cosmetic preservative systems. Kunicka-Styczyńska A. Sikora M, Kalemba D.

[47]*Parasitol Res.* 2012 December; 111(6):2253-63. Evaluation of bioefficacy of three Citrus essential oils against the dengue vector *Aedes albopictus* (Diptera: Culicidae) in correlation to their components enantiomeric distribution. Giatropoulos A, Papachristos D P, Kimbaris A, Koliopoulos G, Polissiou M G, Emmanouel N, Michaelakis A.

[48]Int J Cosmet Sci. 2012 August; 34(4):347-56. Lemon (*Citrus limon*, Burm.f) essential oil enhances the transepidermal release of lipid—(A, E) and water—(B6, C) soluble vitamins from topical emulsions in reconstructed human epidermis. Valgimigli L, Gabbanini S, Berlini E, Lucchi E, Beltramini C, Bertarelli Y L.

[49]Drugs Exp Clin Res.1999; 25(6):281-7. Oxidative stress and antioxidants at skin biosurface: a novel antioxidant from lemon oil capable of inhibiting oxidative damage to the skin. Calabrese V, Scapagnini G, Randazzo S D, Randazzo G, Catalano C, Geraci G, Morganti P.

[50]Drugs Exp Clin Res. 1999; 25(5):219-25. Biochemical studies on a novel antioxidant from lemon oil and its biotechnological application in cosmetic dermatology. Calabrese V, Randazzo S D, Catalano C, Rizza V.

[51]J Med Assoc Thai. 2012 April; 95(4):598-606. The effects of lavender oil inhalation on emotional states, autonomic nervous system, and brain electrical activity. Sayorwan W, Siriponrpanich V, Piriyapunyaporn T, Hongratanaworakit T, Kotchabhakdi N, Ruangrungsi N.

[52]J Cosmet Dermatol 2011 June; 10(2):89-93. Effects of lavender olfactory input on cosmetic procedures. Grunebaum L D, Murdock J, Castanedo-Tardan M P, Baumann L S.

[53]*Psychogeriatrics.* 2009 December; 9(4): 173-9. Effect of aromatherapy on patients with Alzheimer's disease. Jimbo D, Kimura Y, Taniguchi M, Inoue M, Urakami K.

[54]*Behav Brain Res.* 2006 September 25; 172(2):240-9. Lemon oil vapor causes an anti-stress effect via modulating the 5-HT and DA activities in mice. Komiya M, Takeuchi T, Piarada E.

[55]Food Chem Toxicol. 2005 September; 43(9):1381-7. The antimutagenic activity of *Lavandula angustifolia* (lavender) essential oil in the bacterial reverse mutation assay, Evandri M G, Battinelli L, Daniele C, Mastrangelo S, Bolle P, Mazzanti G.

What is claimed is:

1. A syndet for skin cleansing having a pH in the range of from about 5.3 to about 5.8, comprising:
   (a) about 0.01% to about 1% *quillaja* by we,
   (b) about 0.5% to about 2% oat flour;
   (c) about 1% to about 3% beeswax; and
   (d) about 0.5% to about 2% glycerine;
wherein the syndet is solid or liquid at room temperature.

2. The syndet of claim 1, wherein the pH is about 5.5.

3. The syndet of claim 1, wherein the *quillaja* is present at about 0.1% by weight.

4. The syndet of claim 1, further comprising stearic acid and sodium chloride.

5. The syndet of claim 4, wherein the stearic acid is present at about 30% to about 40% by weight and the sodium chloride is present at about 0.5% to about 1% by weight.

6. The syndet of claim 1, further comprising at least one fragrant essential oil.

7. The syndet of claim 6, wherein the at least one fragrant essential oil is selected from the group consisting of bergaptene-free essential lemon oil at about 1.25% weight, thymol at about 0.0005% to about 0.01% by weight and essential lavender oil at about 0.1% to about 1% by weight.

8. The syndet of claim 1, further comprising about 40% to about 50% sodium cocoyl isethionate, about 2% to about 4% cocamidopropyl hydroxysultaine, about 1% to about 3% sodium isethionate, and about 0.5% to about 1% titanium dioxide.

9. A syndet for skin cleansing having a pH in the range of from about 5.3 to about 5.8, comprising:

(a) about 0.01% to about 1% *quillaja* by weight;
(b) about 0.5% to about 2% oat flour;
(c) about 1% to about 3% beeswax;
(d) about 0.5% to about 2% glycerin;
(e) about 0.5% to about 2% bergaptene-free essential lemon oil;
(f) about 0.0001% to about 1% by weight of thymol;
(g) about 0.01% to about 1% by weight of essential lavender oil;
(h) about 40% to about 50% sodium cocoyl isethionate;
(i) about 2% to about 4% cocamidopropyl hydroxysultaine;
(j) about 1% to about 3% sodium isethionate; and
(k) about 0.5% to about 1% titanium dioxide;
wherein the syndet is solid or liquid at room temperature.

10. The syndet of claim 9, wherein the syndet has a pH of about 5.5.

11. A method for cleansing a skin surface comprising applying a syndet to the skin surface, the syndet having a pH in the range of from about 5.3 to about 5.8, wherein the syndet comprises:
(a) about 0.01% to about 1% *quillaja* by weight;
(b) about 0.5% to about 2% oat flour;
(c) about 1% to about 3% beeswax; and
(d) about 0.5% to about 2% glycerine;
wherein the barrier function of the skin surface is not reduced.

12. The method of claim 11, wherein the pH is about 5.5.

13. The method of claim 11, wherein the *quillaja* is present at about 0.1% by weight.

14. The method of claim 11, further comprising stearic acid and sodium chloride.

15. The method of claim 14, wherein the stearic acid is present at about 30% to about 40% by weight and the sodium chloride is present at about 0.5% to about 1% by weight.

16. The method of claim 11, further comprising one or more fragrant essential oils.

17. The method of claim 16, wherein the one or more fragrant essential oils is selected from the group consisting of bergaptene-free essential lemon oil at about 1.25% weight, thymol at about 0.0005% to about 0.01% by weight and essential lavender oil at about 0.1% to about 1% by weight.

18. The method of claim 11, further comprising about 40% to about 50% sodium cocoyl isethionate, about 2% to about 4% cocamidopropyl hydroxysultaine, about 1% to about 3% sodium isethionate, and about 0.5% to about 1% titanium dioxide.

19. A method for cleansing a skin surface comprising applying a syndet to the skin surface, the syndet having a pH in the range of from about 5.3 to about 5.8, wherein the syndet comprises:
(a) about 0.01% to about 1% *quillaja* by weight;
(b) about 0.5% to about 2% oat flour;
(c) about 1% to about 3% beeswax;
(d) about 0.5% to about 2% glycerin;
(e) about 0.5% to about 2% bergaptene-free essential lemon oil;
(f) about 0.0001% to about 1% by weight of thymol;
(g) about 0.01% to about 1% by weight of essential lavender oil;
(h) about 0.40% to about 50% sodium cocoyl isethionate;
(i) about 2% to about 4% cocamidopropyl hydroxysultaine;
(j) about 1% to about 3% sodium isethionate; and
(k) about 0.5% to about 1% titanium dioxide;
wherein the barrier function of the skin surface is not reduced.

20. The method of claim 19, wherein the syndet has a pH of about 5.5.

* * * * *